US 7,445,778 B2
Nov. 4, 2008

(12) United States Patent
Burkly et al.

(10) Patent No.: US 7,445,778 B2
(45) Date of Patent: Nov. 4, 2008

(54) HEDGEHOG AND PATCHED ANTAGONISTS FOR INHIBITING CELL AND TISSUE GROWTH AND DIFFERENTIATION AND USES THEREFOR

(75) Inventors: Linda Burkly, West Newton, MA (US); Li Chun Wang, North Grafton, MA (US)

(73) Assignee: Curis, Inc., Cambridge, MA (US)

(*) Notice: Subject to any disclaimer, the term of this patent is extended or adjusted under 35 U.S.C. 154(b) by 452 days.

(21) Appl. No.: 09/804,490

(22) Filed: Mar. 12, 2001

(65) Prior Publication Data

US 2002/0015702 A1 Feb. 7, 2002

Related U.S. Application Data

(63) Continuation of application No. PCT/US99/20852, filed on Sep. 10, 1999.

(60) Provisional application No. 60/100,037, filed on Sep. 11, 1998.

(51) Int. Cl.
C07K 16/26 (2006.01)
(52) U.S. Cl. .............................. 424/145.1; 530/388.24
(58) Field of Classification Search ............ 530/388.22, 530/300, 350, 399; 514/2; 424/130.1, 178.1, 424/198.1; 436/501
See application file for complete search history.

(56) References Cited

U.S. PATENT DOCUMENTS

| 4,816,567 A * | 3/1989 | Cabilly et al. ............. 530/387.3 |
|---|---|---|
| 5,538,892 A | 7/1996 | Donahoe et al. |
| 5,759,811 A | 6/1998 | Epstein et al. |
| 5,789,543 A | 8/1998 | Ingham et al. |
| 5,789,650 A | 8/1998 | Lonberg et al. |
| 5,837,538 A | 11/1998 | Scott et al. |
| 5,844,079 A | 12/1998 | Ingham et al. |
| 6,027,882 A | 2/2000 | Scott et al. |
| 6,165,747 A | 12/2000 | Ingham et al. |
| 6,172,200 B1 | 1/2001 | Scott et al. |
| 6,261,786 B1 | 7/2001 | Marigo et al. |
| 6,271,363 B1 | 8/2001 | Ingham et al. |
| 6,384,192 B1 | 5/2002 | Ingham et al. |
| 6,429,354 B1 | 8/2002 | Scott et al. |
| 6,551,782 B1 | 4/2003 | Scott et al. |
| 6,576,237 B1 | 6/2003 | Ingham et al. |
| 6,607,913 B1 | 8/2003 | Ingham et al. |
| 6,610,507 B2 | 8/2003 | Scott et al. |
| 6,610,656 B1 | 8/2003 | Ingham et al. |
| 6,630,148 B1 | 10/2003 | Ingham et al. |
| 6,639,051 B2 * | 10/2003 | Wang ........................ 530/350 |
| 6,664,075 B2 | 12/2003 | Ingham et al. |
| 6,884,775 B1 | 4/2005 | Tabin et al. |
| 6,921,646 B2 | 7/2005 | Scott et al. |
| 6,946,257 B1 | 9/2005 | Scott et al. |
| 7,060,450 B1 | 6/2006 | Tabin et al. |
| 7,144,732 B2 | 12/2006 | Ingham et al. |
| 2004/0060568 A1 | 4/2004 | Dudek et al. |
| 2004/0110663 A1 | 6/2004 | Dudek et al. |
| 2005/0054568 A1 | 3/2005 | Ling et al. |

FOREIGN PATENT DOCUMENTS

| WO | WO-95/18856 | 7/1995 |
|---|---|---|
| WO | WO 95/23223 | 8/1995 |
| WO | WO-96/11260 | 4/1996 |

OTHER PUBLICATIONS

Ericson-J et al., Cell 87(661-673)1996.*
Incardona et al., Development 125(3553-3562)1998.*
van-den Heuvel-M et al., Nature 382(547-551)1996.*
Reynolds-NJ et al., Clin Exp. Derm. 27(555-561)2002.*
Leenal Bruckner-Tuderman, Journal of Investigative Dermatology, 114(5)p. 899, 2000.*
Wang-LC et al., Journal of Investigative Dermatology, 114(5)901-908, 2000.*
Alcedo et al., 1996, "The Drosophila smoothened gene encodes a seven-pass membrane protein, a putative receptor for the hedgehog signal", Cell 86:221-232.
Alexandre et al., 1996, "Transcriptional activation of hedgehog target genes in Drosophila is mediated directly by the cubitus interruptus protein, a member of the GLI family of zinc finger DNA-binding proteins", Genes & Dev. 10:2003-2013.
Boerner et al., 1991, "Production of antigen-specific human monoclonal antibodies from in vitro-primed human splenocytes", J. Immunol. 147:86-95.
Bumcrot et al., 1995, "Proteolytic processing yields two secreted forms of sonic hedgehog", Mol. Cell. Biol. 15:2294-2303.
Chang et al., 1994, "Products, genetic linkage and limb patterning activity of a murine hedgehog gene", Development 120:3339-3353.
Co et al., 1991, "Humanized antibodies for antiviral therapy", Proc. Natl. Acad. Sci. USA 88:2869-2873.
Dahmane et al., 1997, "Activation of the transcription factor Gli1 and the Sonic hedgehog signalling pathway in skin tumours", Nature 389:876-880.
Dominguez et al., 1996, "Sending and receiving the hedgehog signal: control by the Drosophila Gli protein Cubitus interruptus", Science 272:1621-1625.
Echelard et al., 1993, "Sonic hedgehog, a member of a family of putative signaling molecules, is implicated in the regulation of CNS polarity", Cell 75:1417-1430.
Ekker et al., 1995, "Patterning activities of vertebrate hedgehog proteins in the developing eye and brain", Curr. Biol. 5:944-955.
Ericson et al., 1996, "Two critical periods of sonic hedgehog signaling required for the specification of motor identity", Cell 87:661-673.
Fan et al., 1995, "Long-range sclerotome induction by sonic hedgehog: direct role of the amino-terminal cleavage product and modulation by the cyclic AMP signaling pathway", Cell 81:457-465.
Hall et al., 1995, "A potential catalytic site revealed by the 1.7-A crystal structure of the amino-terminal signalling domain of Sonic hedgehog", Nature 378:212-216.

(Continued)

*Primary Examiner*—John D Ulm
(74) *Attorney, Agent, or Firm*—Ropes & Gray LLP

(57) ABSTRACT

A method for inhibiting growth or differentiation of an epithelial cell comprising contacting at least an epithelial cell with an effective amount of an agent selected from the group consisting of a hedgehog antagonist and a patched antagonist.

52 Claims, 11 Drawing Sheets

OTHER PUBLICATIONS

Huang and Stollar, 1991, "Construction of representative immunoglobulin variable region cDNA libraries from human peripheral blood lymphocytes without in vitro stimulation", J. Immunol. Meth. 141:227-236.

Johnson and Tabin, 1995, "The long and short hedgehog signaling", Cell 81:313-316.

Jones et al., 1986, "Replacing the complementarity-determining regions in a human antibody with those from a mouse", Nature 321:522-525.

Kohler et al., 1975, "Continuous cultures of fused cells secreting antibody of predefined specificity", Nature 256:495-497.

Lee et al., 1995, "Autoproteolysis in hedgehog protein biogenesis", Science 266:1528-1536.

Marigo et al., 1996, "Biochemical evidence that patched is the Hedgehog receptor", Nature 384:176-179.

Needleman et al., 1970, "A general method applicable to the search for similarities in the amino acid sequence of two proteins", J. Mol. Biol. 48:443-453.

Orlandi et al., 1989, "Cloning immunoglobulin variable domains for expression by the polymerase chain reaction", Proc. Natl. Acad. Sci. USA 86:3833-3837.

Parisi et al., 1998, "The role of the hedgehog/patched signaling pathway in epithelial stem cell proliferation: from fly to human", Cell Res. 8:15-21.

Persson et al., 1991, "Generation of diverse high-affinity human monoclonal antibodies by repertoire cloning", Proc. Natl. Acad. Sci. USA 88:2432-2436.

Porter et al., 1995, "Hedgehog patterning activity: role of a lipophilic modification mediated by the carboxy-terminal autoprocessing domain", Cell 86:21-34.

Porter et al., 1995, "The product of hedgehog autoproteolytic cleavage active in local and long-range signalling", Nature 374:363-366.

Porter et al., 1996, "Cholesterol modification of hedgehog signaling proteins in animal development", Science 274:255-258.

Queen et al., 1989, "A humanized antibody that binds to the interleukin 2 receptor", Proc. Natl. Acad. Sci. USA 86:10029-10033.

Riechmann et al. 1988, "Reshaping human antibodies for therapy", Nature 332:323-327.

St. Jacques et al., 1998, "Sonic hedgehog signaling is essential for hair development", Curr. Biol. 8:1058-1068.

Stone et al., 1996, "The tumour-suppressor gene patched encodes a candidate receptor for Sonic hedgehog", Nature 384:129-134.

Schwartz and Dayhoff, 1978, "Matrices for detecting distant relationships", *Atlas of Protein Sequence and Structure* 5:Suppl. 3 pp. 353-358 (Nat. Biomed. Res. Foundation, Washington, D.C.).

Sultan et al., 1997 "Blockade of CD2-LFA-3 interactions protects human skin allografts in immunodeficient mouse/human chimeras", Nat. Biotechnol. 15:759-762.

Tempest et al., 1991, "Reshaping a human monoclonal antibody to inhibit human respiratory syncytial virus infection in vivo", Biotechnol. 9:266-271.

Therond et al., 1996, "Phosphorylation of the fused protein kinase in response to signaling from hedgehog", Proc. Natl. Acad. Sci. USA 93:4224-4228.

Verhoeyen et al., 1988, "Reshaping human antibodies: grafting an antilysozyme activity", Science 239:1534-1536.

Carter et al. "Allelic loss of chromosomes 16q and 10q in human prostate cancer", PNAS, vol. 87, pp. 8751-8755 (1990).

Fujita et al., "Involvement of Sonic Hedgehog in the Cell Growth of LK-2 Cells, Human Lung Squamous Carcinoma Cells", Biochem. Biophys. Res. Comm., vol. 238, pp. 658-664 (1997).

Green, et al., "Basel cell carcinoma development is associated with induction of the expression of the transcription factor Gli-1", British Journal of Dermatology, vol. 139, pp. 911-915 (1998).

Johnson et al. "Human Homolog of patched, a Candidate Gene for the Basal Cell Nevus Syndrome", Science. vol. 272, pp. 1668-1671 (1996).

Lench et al. "Charaterization of human patched gene line mutations in naevoid basal cell carcinoma syndrome", Hum. Genet., vol. 100, pp. 497-502 (1997).

McGarvey et al. "PTCH gene mutations in invasive transitional cell carcinoma of the bladder", Oncogene, vol. 17, pp. 1167-1172 (1998).

Pepicelli et al. "Sonic hedgehog regulates branching morphogenesis in the mammalian lung", Curr. Biol., vol. 8(19), pp. 1083-1086 (1998).

Podlasek et al. "Prostate Development Requires Sonic Hedgehog Expressed by the Urogenital Sinus Epithelium", Developmental Biology, vol. 209, pp. 28-39 (1999).

Reifenberger et al. "Missense Mutations in SMOH in Sporadic Basal Cell Carcinomas of the Skin and Primitive Neuroectodermal Tumors of the Central Nervous System", Cancer Res., vol. 58, pp. 1798-1803 (1998).

Roberts, et al., "Amplification of the gli Gene in Childhood Sarcomas", Cancer Research, vol. 49, pp. 5407-5413 (1989).

* cited by examiner

5 WEEKS OLD MICE

CTRL    HH-Ab TREATED    CTRL

HH-Ab TREATED E18.5

CTRL E18.5

FIG. 1J HH-Ab TREATED AT d17
FIG. 1I CTRL d17

HH-Ab TREAMENT AFTER BIRTH
AND CONTINUED TO d10

CTRL AT d2

SUSPENDED-TREATMENT MICE   CONTINUOUS-TREATED MICE

5 WEEKS OLD

CONTINUOUS-TREATED MICE   SUSPENDED MICE   CTRL MICE

| FIG. 5A |
| FIG. 5B |
| FIG. 5C |

CONSENSUS SEQUENCE of N-terminal fragments
SEQ ID NO. 4

```
1                                                                    40
CGPGR x1 x2 x3 x4 x5   RR x6 x7 x8 K x9 L x10 P   L x11 YKQF x12 P x13 V   x14 EKTLGASGR 80
x15 EGK x16 x17 R x18 SE   RFK x19 L x20 PNYN   PDIIFKDEEN   x21 GADRLMT x22 R

120
CK x23 x24 x25 NSLAI   x26 VMN x27 WPGVK   LRVTEGWDED   GHH x28 x29 x30 SLHY

160
EGRAVDITTS   DRDR x31 KYG x32 L   ARLAVEAGFD   WVYYES x33 x34 H x25

176
H x36 SVK x37 x38 x39 S x40   AA x41 x42 GG
```

Where:

X1 is either V or G;

X2 is either V, F or P;

X3 is either G or V;

X4 is either S or G;

X5 is either R or K;

X6 is either P, H or Y;

X7 is either P or A;

X8 is either R or K;

X9 is any amino acid;

X10 is either V or T;

X11 is either A or L;

X12 is either S, I or V;

X13 is either N or G;

X14 is either P or A;

X15 is either Y or A;

X16 is either I or V;

X17 is either A or S;

X18 is either S, N or G;

X19 is either E or D;

X20 is either T or V;

FIG. 5B

X21 is either T or S;

X22 is either Q or E;

X23 is either D or E;

X24 is either R or K;

X25 is either L or V;

X26 is either S or A;

X27 is either Q or M;

X28 is either S or A;

X29 is either E or Q;

X30 is either E or D;

X31 is either N or S;

X32 is either N or M;

X33 is either K or R;

X34 is either A or N;

X35 is either V or I;

X36 is either C or V;

X37 is either S or A;

X38 is either E or D;

X39 is either H or N;

X40 is either A, V or L;

X41 is either K or R; and

X42 is either T, S or A.

FIG. 5C

HEDGEHOG AND PATCHED ANTAGONISTS FOR INHIBITING CELL AND TISSUE GROWTH AND DIFFERENTIATION AND USES THEREFOR

This application is a continuation of and claims priority to PCT US99/20852, filed Sep. 10, 1999, which claims priority to U.S. provisional application Ser. No. 60/100,037, filed Sep. 11, 1998, the disclosures of which are hereby incorporated by reference in their entirety.

BACKGROUND OF THE INVENTION

Members of the Hedgehog ("hh") family of signaling molecules mediate many important short-and long range patterning processes during invertebrate and vertebrate development.

To date, the combined screening of mouse genomic and cDNA libraries has identified three mammalian hh counterparts referred to as Desert hedgehog (Dhh), Sonic hedgehog (Shh) and Indian hedgehog (Ihh), which also exist in other mammals as well as in fish and birds. Other members include Moonrat hedgehog (Mhh), as well as chicken Sonic hh and zebrafish Sonic hh. Mouse and chicken Shh and mouse Ihh genes encode glycoproteins which undergo cleavage, yielding an amino terminal fragment of about 20 kDa and a carboxy terminal fragment of about 25 kDa. The 20 kDa fragment has the consensus sequence SEQ ID NO: 1 (FIG. 5). Publications disclosing these sequences, as well as their chemical and physical properties, include Hall et al., (1995) *Nature* 378, 212-216; Ekker et al., (1995) *Current Biology* 5, 944-955; Fan et al., (1995) *Cell* 81, 457-465; Chang et al., (1994) *Development* 120, 3339-3353; Echelard et al., (1993) *Cell* 75, 1414-1430; and PCT Patent Application WO 9523223 (Jessell, Dodd, Roelink and Edlund).

Human Shh is synthesized as a 45 kDa precursor protein that is also autocatalytically cleaved to yield: (I) a 20 kDa N-terminal fragment that is responsible for all known hedgehog signaling activity; and (II) a 25 kDa C-terminal fragment that contains the autoprocessing activity (Lee, J. J., et al. (1994) *Science* 266, 1528-1536; Bumcrot, D. A., et al. (1995), *Mol. Cell Biol.* 15, 2294-2303; Porter, J. A., et al. (1995) *Nature* 374, 363-366).

The N-terminal fragment consists of amino acid residues 24-197 of the full-length precursor sequence. The N-terminal fragment remains membrane-associated through the addition of a cholesterol at its C-terminus (Porter, J. A., et al. (1996) *Science* 274, 255-258; Porter, J. A., et al. (1995) *Cell* 86, 21-34). This cholesterol is critical for restricting the tissue localization of the hedgehog signal. The addition of the cholesterol is catalyzed by the C-terminal domain during the processing step. As a result of the membrane tethering, a high local concentration of N-terminal hedgehog peptide is generated on the surface of the hedgehog producing cells.

The hedgehog proteins regulate various aspects of embryonic development both in vertebrates and invertebrates (for reviews see Perrimon, N. (1995) *Cell* 80, 517-520 and Johnson, R. L., and Tabin, C. (1995) *Cell* 81, 313-316). The most well-characterized hedgehog protein is Sonic hedgehog (Shh), involved in anterior-posterior patterning, formation of an apical ectodermal ridge, hindgut mesoderm, spinal column, distal limb, rib development, and lung development, and inducing ventral cell types in the spinal cord, hindbrain and forebrain (3-8). While the mechanism of action of hedgehog proteins is not fully understood, the most recent biochemical and genetic data suggest that the receptor for Shh is the product of the tumor suppressor gene, patched (Marigo, V., et al. (1996) *Nature* 384, 176-179; Stone, D. M., et al. (1996) *Nature* 384, 129-134) and that other proteins; smoothened (Stone, D. M., et al. (1996) *Nature* 384, 129-134; Alcedo, J., et al. (1996) *Cell* 86, 221-232), *Cubitus interruptus* (Dominguez, M., et al. (1996) *Science* 272, 1621-1625; Alexandre, C., et al. (1996) *Genes & Dev.* 10, 2003-2013), and fused (Therond, P. P., et al. (1996) *Proc. Natl. Acad. Sci. USA* 93, 4224-4228) are involved in the hedgehog signaling pathway. The interaction of a hedgehog protein with one of its cognate receptors, patched (ptc), sets in motion a cascade involving the activation and inhibition of downstream effectors, the ultimate consequence of which is, in some instances, a detectable change in the transcription or translation of a gene. Hedgehog and its cognate receptor patched (ptc) are expressed in the epithelial and/or mesenchymal cell components of the skin (i.e., the hair follicle). See Parisi et al., (1998) *Cell Res* 8, 15-21; St. Jacques et al., (1998) *Current Biology*, 8, 1058-1068; and Dahmane et al., (1997) *Nature*, 389, 876-880. The two-way interaction between epithelial and the dermal mesenchymal cells directs the subsequent development of hair follicles. Disrupting this interaction might lead to a modulation of proliferation and/or differentiation events that give rise to hair and/or epithelial tissue structures such as the gut.

SUMMARY OF THE INVENTION

One aspect of the invention is a method for inhibiting growth or differentiation of an epithelial cell comprising contacting at least the epithelial cell with an effective amount of an agent selected from the group consisting of a hedgehog antagonist and a patched antagonist. The hedgehog antagonist can be an anti-hedgehog antibody homolog selected from the group consisting of a human antibody, a chimeric antibody, a humanized antibody and fragments thereof. The patched antagonist can be an anti-patched antibody homolog selected from the group consisting of a human antibody, a chimeric antibody, a humanized antibody and fragments thereof. Further antagonists of the invention include a hedgehog mutant that binds to a hedgehog receptor but does not elicit hedgehog-mediated signaling.

Another aspect is a method for inhibiting growth of an epithelial tissue comprising contacting at least the epithelial tissue with an amount of an agent effective to inhibit proliferation of at least the epithelial cells in the tissue, wherein the agent is selected from the group consisting of a hedgehog antagonist and a patched antagonist.

Yet another aspect is a method for inhibiting growth of hair on an animal, comprising treating the animal with an amount of an agent effective to inhibit growth of hair, wherein the agent is selected from the group consisting of a hedgehog antagonist and a patched antagonist which inhibit proliferation of hair follicle keratinocytes. In another aspect of the invention, the anti-hedgehog antibody homolog is an antibody homolog that binds to a Sonic hedgehog protein, an Indian hedgehog protein and/or a Desert hedgehog protein.

A further aspect of the invention is a method for inhibiting the proliferation of hair follicle cells, comprising contacting the cells with a hedgehog antagonist or a patched antagonist in an amount effective to decrease the proliferation of the hair follicle cells

DESCRIPTION OF THE FIGURES

FIGS. 1B and 1C are histological sections through the epithelium of untreated mice and treated mice, respectively, at stage E15.5.

FIGS. 1I and 1J are histological sections through the epithelium of untreated mice and treated mice, respectively, at day 17 after birth.

FIG. 5A-5C depicts the consensus amino acid sequence of the N-terminal domain of vertebrate hedgehog protein.

DETAILED DESCRIPTION OF THE INVENTION

Figure 1B:
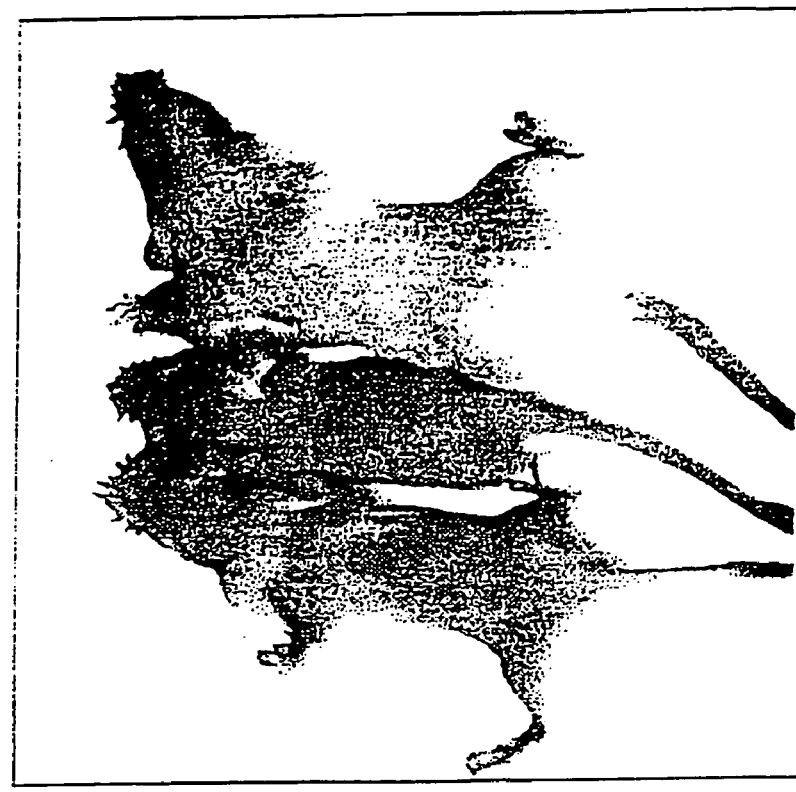
FIG. 1A is a picture of treated and untreated mice when treatments were done prenatally and FIG. 1B are pictures of mice when treatements were continued after birth for every other day.

The present application is directed to the discovery that preparations of hedgehog and patched antagonists can be used to control the formation and/or maintenance of epithelial and/or mesenchymal tissue. In general, the method of the present invention comprises contacting an epithelial cell and/or a mesenchymal cell with an amount of a hedgehog or patched antagonist (defined infra) which produces a nontoxic response by the cell of inhibition of growth and/or differentiation of the mesenchymal and/or epithelial cell. The subject method can be most preferably carried out on epithelial cells which may be either dispersed in culture or a part of an intact tissue or organ. Moreover, the method can be performed on cells which are provided in culture (in vitro), or on cells in a whole animal (in vivo).

In one aspect, the present invention provides pharmaceutical preparations and methods for controlling the proliferation and/or differentiation of mesenchymally and/or epithelially-derived cells utilizing, as an active ingredient, a hedgehog or patched antagonist. In the preferred embodiment, the invention contemplates using hedgehog or patched antagonists to control the proliferation and/or differentiation of epithelial cells or tissues.

The preferred invention also relates to methods of controlling proliferation of epithelial-derived tissue by use of the pharmaceutical preparations of the invention.

In another aspect of the preferred invention, antagonist preparations of the invention can be used to effect the growth of hair, as for example cosmetic removal of hair (depilation) whereby hair growth is inhibited.

In certain embodiments, the antagonists may be applied to the treatment or prevention of a variety hyperplastic or neoplastic conditions. The method can find application for the treatment or prophylaxis of, e.g., psoriasis; keratosis: acne; comedogenic lesions; folliculitis and pseudofolliculitis; keratoacanthoma; callosities; Darier's disease; ichthyosis; lichen planus; molluscous contagiosum: melasma; Fordyce disease; and keloids or hypertrophic' scars. Certain of the formulations of the present invention may also be used as part of treatment regimens in auto-immune diseases for affecting proliferative manifestations of the disorder, as for example, part of a treatment for aphthous ulcers, pemphigus such as pemphigus vulgaris, pemphigus foliaceus, pemphigus vegetans or pemphigus erythematous, epidermolysis, lupus lesions or desquamative lesions.

The subject treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

II. Definitions

For convenience, certain terms employed in the specification, examples, and appended claims are collected here.

"Normal skin epidermis" is a complex epithelial tissue containing keratinocytes that are proliferating, differentiating and desquamating, and is stratified such that morphological functional changes in the keratinocytes occur in an orderly progression. The normal epidermis is maintained in a dynamic steady state as proliferation of keratinocytes continually compensates for the loss of cells which are shed from the surface of the skin. Within the epidermis, proliferation takes place in the basal layer of keratinocytes that are attached to the underlying basement membrane, and cells undergo ten-ninal differentiation as they migrate through the suprabasal layers, finally being shed from the tissue surface as dead, cornified squames. Three subpopulations of basal keratinocytes have been defined by cell kinetic analysis: stem cells, transit-amplifying cells, and committed cells. Stem cells retain a high capacity for self-renewal throughout adult life and are ultimately responsible for epidermal maintenance and repair. The progeny of stem cells can either be stem cells themselves or cells known as transit-amplifying cells. Transit-amplifying cells divide a small number of times, but have a high probability of producing daughters that withdraw irreversibly from the cell cycle and are committed to differentiate terminally.

"amino acid"—a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

"protein"—any polymer consisting essentially of any of the 20 amino acids. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"vesicle"—refers to any aggregate of lipophilic molecules. The vesicle may be obtained from a biologic source (e.g., a lipid bilayer such as a cell membrane or a cholic acid-derived detergent preparation) or from a non-biologic source (e.g., a non-biologic detergent vesicle as described in Section V). The shape, type, and configuration of the vesicle is not intended to limit the scope of this invention.

"genetic fusion"—refers to a co-linear, covalent linkage of two or more proteins or fragments thereof via their individual peptide backbones, through genetic expression of a polynucleotide molecule encoding those proteins.

"mutant"—any change in the genetic material of an organism, in particular any change (i.e., deletion, substitution, addition, or alteration) in a wild-type polynucleotide sequence or any change in a wild-type protein.

"wild-type"—the naturally-occurring polynucleotide sequence of an exon of a protein, or a portion thereof, or protein sequence, or portion thereof, respectively, as it normally exists in vivo.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulphate, and 100 µg/ml denatured, sonicated salmon sperm DNA at 65° C. for 12-20 hours, and washing with 75 mM NaCl/7.5 mM sodium citrate (0.5×SSC)/1% SDS at 65° C. Lower stringency conditions may, for example, include hybridizing with plaque screen buffer, 10% dextran sulphate and 110 µg/ml denatured, sonicated salmon sperm DNA at 55° C. for 12-20 hours, and washing with 300 mM NaCl/30mM sodium citrate (2.0×SSC)/1% SDS at 55° C. See also Current Protocols in Molecular Biology, John Wiley & Sons, Inc. New York, Sections 6.3.1-6.3.6, (1989).

"expression control sequence"—a sequence of polynucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired polypeptide encoded by the polynucleotide sequence.

"expression vector"—a polynucleotide, such as a DNA plasmid or phage (among other common examples) which allows expression of at least one gene when the expression vector is introduced into a host cell. The vector may, or may not, be able to replicate in a cell.

"Isolated" (used interchangeably with "substantially pure")—when applied to nucleic acid i.e., polynucleotide sequences, that encode polypeptides, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as an expression vector, or a portion thereof): or (ii) is linked to a nucleic acid or other chemical moiety other than that to which it is linked in nature; or (iii) does not occur in nature. By "isolated" it is further meant a polynucleotide sequence that is: (i) amplified in vitro by, for example, polymerase chain reaction (PCR); (ii) chemically synthesized; (iii) recombinantly produced by cloning; or (iv) purified, as by cleavage and gel separation.

Thus, "substantially pure nucleic acid" is a nucleic acid which is not immediately contiguous with one or both of the coding sequences with which it is normally contiguous in the naturally occurring genome of the organism from which the nucleic acid is derived. Substantially pure DNA also includes a recombinant DNA which is part of a hybrid gene encoding additional hedgehog sequences.

"Isolated" (used interchangeably with "substantially pure")—when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is: (i) chemically synthesized; or (ii) expressed in a host cell and purified away from associated proteins. The term generally means a polypeptide that has been separated from other proteins and nucleic acids with which it naturally occurs. Preferably, the polypeptide is also separated from substances such as antibodies or gel matrices (polyacrylamide) which are used to purify it.

"heterologous promoter"—as used herein is a promoter which is not naturally associated with a gene or a purified nucleic acid.

"Homologous"—as used herein is synonymous with the term "identity" and refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The percentage homology between two sequences is a function of the number of matching or homologous positions shared by the two sequences divided by the number of positions compared×100. For instance, if 6 of 10 of the positions in two sequences are matched or are homologous, then the two sequences are 60% homologous. By way of example, the DNA sequences CTGACT and CAGGT share 50% homology (3 of the 6 total positions are matched). Generally, a comparison is made when two sequences are aligned to give maximum homology. Such alignment can be provided using, for instance, the method of Needleman et al., *J. Mol Biol.* 48: 443453 (1970), implemented conveniently by computer programs such as the Align program (DNAstar, Inc.). Homologous sequences share identical or similar amino acid residues, where similar residues are conservative substitutions for, or "allowed point mutations" of, corresponding amino acid residues in an aligned reference sequence. In this regard, a "conservative substitution" of a residue in a reference sequence are those substitutions that are physically or functionally similar to the corresponding reference residues, e.g., that have a similar size, shape, electric charge. chemical properties, including the ability to form covalent or hydrogen bonds, or the like. Particularly preferred conservative substitutions are those fulfilling the criteria defined for an "accepted point mutation" in Dayhoff et al., 5: Atlas of Protein Sequence and Structure, 5: Suppl. 3, chapter 22: 354-352, Nat. Biomed. Res. Foundation, Washington, D.C. (1978).

A "hedgehog protein" of the invention is defined in terms of having at least a portion that consists of the consensus amino acid sequence of SEQ ID NO: 1.

The terms "peptide(s)", "protein(s)" and "polypeptide(s)" are used interchangeably herein. The terms "polynucleotide sequence" and "nucleotide sequence" are also used interchangeably herein. The term "Hedgehog fragment" is used interchangeably with "Hedgehog".

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Harnes and S. J. Higgins, eds.), 1984; Culture of Animal Cells (R. I. Freshney, ed). Alan R. Liss, Inc., 1987: Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

The term "patched" or "ptc" refers to a family of related transmembrane proteins which have been implicated in the signal transduction induced by contacting a cell with a hedgehog protein. For example, the mammalian ptc family includes ptc1 and ptc2.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, which that characteristically found lining hollow organs that are subject to great mechanical change due to contraction and distention, e.g. tissue which represents a transition between stratified squamous and columnar epithelium The term "epithelialization" refers to healing by the growth of epithelial tissue over a denuded surface.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

The term "nail" refers to the horny cutaneous plate on the dorsal surface of the distal end of a finger or toe.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "hair" refers to a threadlike structure, especially the specialized epidermal structure composed of keratin and developing from a papilla sunk in the corium, produced only by mammals and characteristic of that group of animals. Also, the aggregate of such hairs. A "hair follicle" refers to one of the tubular-invaginations of the epidermis enclosing the hairs, and from which the hairs grow; and "hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

"Dental tissue" refers to tissue in the mouth which is similar to epithelial tissue, for example gum tissue. The method of the present invention is useful for treating periodontal disease.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. Another example is "epidermolysis", which refers to- a loosened state of the epidermis with formation of blebs and bullae either spontaneously or at the site of trauma.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Another carcinomatous epithelial growth is "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle.

The term "keratosis" refers to proliferative skin disorder characterized by hyperplasia of the horny layer of the epidermis. Exemplary keratotic disorders include keratosis follicularis, keratosis palmaris et plantaris, keratosis pilaris, and actinic keratosis.

As used herein, "proliferating" and "proliferation" refer to cells undergoing mitosis.

As used herein, "transformed cells" refers to cells which have spontaneously converted to a state of unrestrained growth, i.e., they have acquired the ability to crow through an indefinite number of divisions in culture. Transfected cells may be characterized by such terms as neoplastic, anaplastic and/or hyperplastic, with respect to their loss of growth control.

As used herein, "immortalized cells" refers to cells which have been altered via chemical and/or recombinant means such that the cells have the ability to grow through an indefinite number of divisions in culture.

A "patient" or "subject" to be treated by the subject method can mean either a human or non-human animal.

The term "cosmetic preparation" refers to a pharmaceutical preparation which is formulated for topical administration.

An "effective amount" of an antagonist of the invention with respect to the subject method of treatment, refers to an amount of, e.g., a anti-hedgehog antibody homolog in a preparation which, when applied as part of a desired dosage regimen brings about a change in the rate of cell proliferation and/or the state of differentiation of a cell so as to produce an amount of epithelial and/or mesenchymal cell proliferation according to clinically acceptable standards for the disorder to be treated or the cosmetic purpose.

The "growth state" of a cell refers to the rate of proliferation of the cell and the state of differentiation of the cell.

III Utilities

Overview

The subject method has wide applicability to the treatment or prophylaxis of disorders afflicting epithelial tissue, as well as in cosmetic uses. In general, the method can be characterized as including a step of administering to an animal an amount of a ptc or hedgehog antagonist effective to supress or otherwise inhibit the proliferative state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

For the purposes of the invention a "hedgehog antagonist" or "patched antagonist" refers to an agent, e.g., a polypeptide such as an anti-hedgehog or anti-patched antibody which can inhibit or block hedgehog and/or patched-mediated binding or which can otherwise modulate hedgehog and/or patched function, e.g., by inhibiting or blocking hedgehog-ligand mediated hedgehog signal transduction. Such an antagonist of the hedgehog/patched interaction is an agent which has one or more of the following properties: (1) it coats, or binds to, a hedgehog on the surface of a hedgehog bearing or secreting cell with sufficient specificity to inhibit a hedgehog-ligand/hedgehog interaction, e.g., the hedgehog/patched interaction; (2) it coats, or binds to, a hedgehog on the surface of a hedgehog-bearing or secreting cell with sufficient specificity to modify, and preferably to inhibit, transduction of a hedgehog-mediated signal e.g., hedgehog/patched-mediated signaling; (3) it coats, or binds to, a hedgehog ligand, (e.g., patched) in or on cells with sufficient specificity to inhibit the hedgehog/patched interaction; (4) it coats, or binds to, a hedgehog ligand (e.g., patched) in or on cells with sufficient specificity to modify, and preferably to inhibit, transduction of hedgehog ligand mediated hedgehog signaling, e.g., patched-mediated hedgehog signaling. In preferred embodiments the antagonist has one or both of properties 1 and 2. In other preferred embodiments the antagonist has one or both of properties 3 and 4. Moreover, more than one antagonist can be administered to a patient, e.g., an agent which binds to hedgehog can be combined with an agent which binds to patched.

As discussed herein, the antagonists used in methods of the invention are not limited to a particular type or structure of molecule so that, for purposes of the invention, any agent capable of binding to hedgehog antigens and which effectively blocks or coats hedgehog is considered to be an equivalent of the antagonists used in the examples herein.

For example, antibodies or antibody homologs (discussed below) as well as other molecules such as soluble forms of the natural binding proteins for hedgehog are useful. Soluble forms of the natural binding proteins for hedgehog include soluble patched peptides, patched fusion proteins, or bifunctional patched/Ig fusion proteins. For example, a soluble form of patched or a fragment thereof may be administered to bind to hedghog, and preferably compete for a hedgehog binding site on cells, thereby leading to effects similar to the administration of antagonists such as anti-hedgehog antibodies. In particular, soluble hedgehog mutants that bind patched but do not elicit hedgehog-dependent signaling are included within the scope of the invention. Such hedgehog mutants can act as competitive inhibitors of wild type hedgehog protein and are considered "antagonists".

In another example, patched, or a fragment thereof which is capable of binding to hedgehog on cells, can be fused to a second peptide, e.g., a peptide which increases the solubility or the in vivo lifetime of the patched moiety. The second peptide can be a fragment of a soluble peptide, preferably a human peptide, more preferably a plasma protein, or a member of the immunoglobulin superfamily. In particularly preferred embodiments the second peptide is IgG or a portion or fragment thereof, e.g., the human IgG1 heavy chain constant region and includes, at least the hinge, CH2 and CH3 domains.

The most preferred embodiments are patched or hedgehog antagonists used in the method of the invention to bind to, including block or coat, cell-surface hedgehog or patched. These compositions include monoclonal antibody such an an anti-hedgehog or anti-patched antibody homolog. Preferred antibodies and homologs for treatment, in particular for human treatment, include human antibody homologs, humanized antibody homologs, chimeric antibody homologs, Fab, Fab', F(ab')2 and F(v) antibody fragments, and monomers or dimers of antibody heavy or light chains or mixtures thereof. Thus, monoclonal antibodies against hedgehog are the preferred binding agent in the method of the invention.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., hedgehog or patched). The component polypeptides of an antibody homolog composed of more than one polypeptide may optionally be disulfide-bound or otherwise covalently crosslinked.

Accordingly, therefore, "antibody homologs" include intact immunoglobulins of types IgA, IgG, IgE, IgD, IgM (as well as subtypes thereof), wherein the light chains of the immunoglobulin may be of types kappa or lambda.

"Antibody homologs" also include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain. In another aspect the invention features a variant of a chimeric molecule which includes: (1) a hedgehog targeting moiety, e.g., a patched moiety capable of binding to antigen (i.e., hedgehog); (2) optionally, a second peptide, e.g., one which increases solubility or in vivo life time of the hedgehog targeting moiety, e.g., a member of the immunoglobulin super family or fragment or portion thereof, e.g., a portion or a fragment of IgG, e.g., the human IgGI heavy chain constant region, e.g., CH2 and CH3 hinge regions; and a toxin moiety. The hedgehog targeting moiety can be any naturally occurring hedgehog ligand or fragment thereof, e.g., a patched peptide or a similar conservatively substituted amino acid sequence. A preferred targeting moiety is a soluble patched fragment. The chimeric molecule can be used to treat a subject, e.g., a human, at risk for disorder related to proliferation of epithelial cells such as hair follicles and the like.

As used herein, a "human antibody homolog" is an antibody homolog produced by recombinant DNA technology, in which all of the amino acids of an immunoglobulin light or heavy chain that are derived from a human source.

Methods of Making Anti-Hedgehog and Anti-Patched Antibody Homologs: The technology for producing monoclonal antibody homologs is well known. Briefly, an immortal cell line (typically myeloma cells) is fused to lymphocytes (typically splenocytes) from a mammal immunized with whole cells expressing a given antigen, e.g., hedgehog, and the culture supernatants of the resulting hybridoma cells are screened for antibodies against the antigen. See, generally, Kohler et at., 1975, Nature 265: 295-497, "Continuous Cultures of Fused Cells Secreting Antibody of Predefined Specificity".

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-hedgehog antibodies may be identified by immunoprecipitation of 125I-labeled cell lysates from hedgehog-expressing cells. Anti-hedgehog antibodies may also be identified by flow cytometry, e.g., by measuring fluorescent staining of antibody-expressing cells incubated with an antibody believed to recognize hedgehog. The lymphocytes used in the production of hybridoma cells typically are isolated from immunized mammals whose sera have already tested positive for the presence of anti-hedgehog antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively ftised myeloma cells (unfused splenocytes die after several days because they are not transformed). Hybridomas producing a desired antibody are detected by screening the hybridoma culture supernatants. For example, hybridomas prepared to produce anti-hedgehog antibodies may be screened by testing the hybridoma culture supernatant for secreted antibodies having the ability to bind to a recombinant hedgehog-expressing cell line.

To produce anti-hedgehog antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-hedgehog antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several mouse anti-hedgehog monoclonal antibodies have been previously described (see Example)

Fully human monoclonal antibody homologs against hedgehog or patched are another preferred binding agent which may block or coat hedgehog or patched antigens in the method of the invention. In their intact form these may be prepared using in vitro-primed human splenocytes, as described by Boemer et al., 1991, J. Immunol. 147:86-95, "Production of Antigen-specific Human Monoclonal Antibodies from Ii Vitro-Primed Human Splenocytes".

Alternatively, they may be prepared by repertoire cloning as described by Persson et al., 1991, Proc. Nat. Acad. Sci. USA 88: 2432-2436, "Generation of diverse high-affinity human monoclonal antibodies by repertoire cloning" and Huang and Stollar, 1991, J. Immunol. Methods 141: 227-236, "Construction of representative immunoglobulin variable region cDNA libraries from human peripheral blood lymphocytes without in vitro stimulation". U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Yet another preferred binding agent which may block or coat hedgehog or patched antigens in the method of the invention is a humanized recombinant antibody homolog having the capability of binding to a hedgehog or patched protein. Following the early methods for the preparation of chimeric antibodies, a new approach was described in EP 0239400 (Winter et al.) whereby antibodies are altered by substitution of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping". (Riechmann et al., 1988 Nature 332: 323-327, "Reshaping human antibodies for therapy"; Verhoeyen et al., 1988, Science 239: 1534-1536, "Reshaping of human antibodies using CDR-grafting in Monoclonal Antibodies".

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986 Nature 321: 522-525, "Replacing the complementarity-determining regions in a human antibody with those from a mouse"; Riechmann, 1988, Nature 332:323-327, "Reshaping human antibodies for therapy"; Queen et al., 1989, Proc. Nat. Acad. Sci. USA 86:10029, "A humanized antibody that binds to the interleukin 2 receptor" and Orlandi et al., 1989, Proc. Natl. Acad. Sci. USA 86:3833 "Cloning Immunoglobulin variable domains for expression by the polymerase chain reaction".

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In a number of cases, it appears to be critical to alter residues in the framework regions of the acceptor antibody in order to obtain binding activity.

Queen et al., 1989, Proc. Nat. Acad. Sci. USA 86: 10029-10033, "A humanized antibody that binds to the interleukin 2 receptor" and WO 90/07861 (Protein Design Labs Inc.) have described the preparation of a humanized antibody that contains modified residues in the framework regions of the acceptor antibody by combining the CDRs of a murine mAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [supra]) and also for antibodies specific for herpes simplex virus (HSV) (Co. et al., 1991. Proc. Nat. Acad. Sci. USA 88: 2869- 2873, "Humanised antibodies for antiviral therapy".

According to the above described two step approach in WO 90/07861, Queen et al. outlined several criteria for designing humanized immunoglobulins. The first criterion is to use as the human acceptor the framework from a particular human immunoglobulin that is usually homologous to the non-human donor immunoglobulin to be humanized, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRS.

One may use a different approach (see Tempest, 1991, Biotechnology 9: 266-271, "Reshaping a human monoclonal antibody to inhibit human respiratory syncytial virus infection in vivo") and utilize, as standard, the V region frameworks derived from NEWM and REI heavy and light chains respectively for CDR-grafting without radical introduction of mouse residues. An advantage of using the Tempest et al., 1991 approach to construct NEWM and REI based humanized antibodies is that the 3dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody.

Preferred antagonists useful in the present invention include chimeric recombinant and humanized recombinant antibody homologs ( i.e., intact immunoglobulins and portions thereof) with hedgehog or patched specificity.

Utilities

Preparations of hedgehog or patched antagonist described herein can be used to inhibit lens epithelial cell proliferation to prevent post-operative complications of extracapsular cataract extraction. Cataract is an intractable eye disease and the treatment of cataract is attained by surgical operations. Extracapsular lens extraction has become the method of choice for removing cataracts. However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapslilar lens extraction. To inhibit secondary cataract formation, the subject method provides a means for inhibiting proliferation of the remaining lens epithelial cells. For example, such cells can be induced to remain quiescent by instilling a solution containing an antiproliferative hedgehog or patched antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

In another aspect of the invention, the subject method can be used in conjunction with various periodontal procedures in which control of epithelial cell proliferation in and around periodontal tissue is desired.

In another embodiment, antagonist therapeutics can find application in the treatment of peridontal disease. It is estimated that in the United States alone, there are in excess of 125 million adults with periodontal disease in varying forms. Periodontal disease starts as inflammatory lesions because of specific bacteria localizing in the area where the gingiva attaches to the tooth. Inflammation in the connective tissue stimulates the following changes in the epithelial lining of the sulcus and in the epithelial attachment: increased mitotic activity in the basal epithelial layer; increased producing of keratin with desquamation; cellular desquamation adjacent to the tooth surface tends to deepen the pocket; epithelial cells of the basal layer at the bottom of the sulcus and in the area of attachment proliferate into the connective tissue and break up of the gingival fibers begins to occur, wherein dissolution of the connective tissue results in the formation of an open lesion. The application of hedgehog preparations to the periodontium can be used to inhibit proliferation of epithelial tissue and thus prevent further periodontoclastic development.

Yet another aspect of the present invention relates to the use of antagonists such as anti-hedgehog antibody homologs to control hair growth. Hair is basically composed of keratin, a tough and insoluble protein. Each individual hair comprises a cylindrical shaft and a root, and is contained in a follicle, a flask-like depression in the skin. The bottom of the follicle contains a finger-like projection termed the papilla, which consists of connective tissue from which hair-grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells. As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for reducing hair growth can be carried out by inhibiting, respectively, the proliferation of these stem cells.

In one embodiment, the subject method provides a means for altering the dynamics of the hair growth cycle to directly inhibit proliferation of hair follicle cells (particularly stem cells of the hair follicle) and/or directly modulate differentiation of the stem cells. The subject compositions and method can be used to decrease hair follicle size and the rate of hair growth in warm-blooded animals, such as humans, e.g., by inhibiting proliferation of hair follicle stem cells. In one embodiment, the method comprises administering to the skin in the area in which inhibition of hair growth is desired an amount of hedgehog or ptc antagonist (e.g., an anti-hedgehog antibody homolog) sufficient to decrease hair follicle size and/or the rate of hair growth in the animal. Typically, the composition will be administered topically as a cream, and will be applied on a daily basis until hair growth inhibition is observed and for a time thereafter sufficient to maintain the desired amount of hair growth.

For instance, the present method can be used in the treatment of trichosis characterized by abnormally rapid or dense growth of hair, e.g. hypertrichosis. In an exemplary embodiment, antagonists can be used to manage hirsutism, a disorder marked by abnormal hairiness. The subject method can also provide a process for extending the duration of depilation. Moreover, because a hedgehog antagonist will often be cytostatic to epithelial cells, rather than cytotoxic, such agents can be used to protect hair follicle cells from cytotoxic agents which require progression into S-phase of the cell-cycle for efficacy, e.g. radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, treatment can also be removed with concommitant relief of the inhibition of follicle cell proliferation. (See Example 1, section 4).

The subject method can also be used in the treatment of folliculitis, such as folliculitis decalvans, folliculitis uterythematosa reticulate or keloid folliculitis. For example, a cosmetic preparation of an hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, antagonists of the invention can be used to inhibit differentiation of epithelial-derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical antagonists of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or noninflammatory components. To illustrate, therapeutic preparations e.g., which promotes quiescense or differentiation can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject antagonist preparations. Actinic keratoses, for example, are superficial inflammatory premalignant tumors arising on sun-exposed and irradiated skin. Current therapies include excisional and cryosurgery. These treatments are painful, however, and often produce cosmetically unacceptable scarring. Accordingly, treatment of keratosis, such as actinic keratosis, can include application, preferably topical, of an antagonist composition in amounts sufficient to inhibit hyperproliferation of epidermal cells of the lesion.

Acne represents yet another dermatologic ailment which may be treated with an embodiment of the subject method. Acne vulgaris, for instance, is a multifactorial disease most commonly occurring in teenagers and young adults, and is characterized by the is appearance of inflammatory and noninflammatory lesions on the face and upper trunk. Treatment with antagonist form of a hedgehog or ptc, particularly topical preparations, may be useful for preventing the transitional features of the ducts, e.g. hypercornification, which lead to lesion formation. The subject treatment may further include, for example, antibiotics, retinoids and antiandrogens.

VI. Pharmaceutical Preparations

In this method according to the first aspect of the invention, antagonists such as anti-hedgehog antibody homologs are administered parenterally. The term "parenteral" as used herein includes subcutaneous, intravenous, intramuscular, intra-articular, intra-synovial, intrasternal, intrathecal, intrahepatic, intralesional and intracranial injection or infusion techniques.

The antibody homologs are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris(hydroxymethyl)methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1.3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions.

The pharmaceutical compositions of this invention may be given orally. If given orally, they can be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component. As appropriate compositions for topical application there may be cited all compositions usually employed for topically administering therapeutics, e.g., creams, genies, dressings, shampoos, tinctures, pastes, ointments, salves, powders, liquid or semiliquid formulation and the like. Application of said compositions may be by aerosol e.g. with a propellant such as nitrogen carbon dioxide, a freon, or without a propellant such as a pump spray, drops, lotions, or a semisolid such as a thickened composition which can be applied by a swab. In particular compositions, semisolid compositions such as salves, creams, pastes, genies, ointments and the like will conveniently be used.

The pharmaceutical preparations of the present invention can be used, as stated above, for the many applications which can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. anti inflammatory agents, antibacterials, antifungals, disinfectants, vitamins, sunscreens, antibiotics, or other anti-acne agents. Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold Linder the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxyanisole, propyl gallate, and citric acid; examples of chelating agents include disodium edentate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid. For preparing ointments, creams, toilet waters, skin milks, and the like, typically from 0.01 to 10% in particular from 0.1 to 5% and more in particular from 0.2 to 2.5% of the active ingredient, will be incorporated in the compositions. In ointments or creams, the carrier for example consists of 1 to 20%, in particular 5 to 15% of a humectant, 0.1 to 10% in particular from 0. 5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2-15% of a humectant, 0 to 80% of an oil, very small (<2%) amounts of preservative, coloring agent and/or perfume, and water. In a toilet water, the carrier for example consists of 2 to 10% of a lower alcohol, 0. 1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10-50% of oil, 1 to 10% of surfactant, 50-80% of water and 0 to 3% of preservative and/or perfume. In the aforementioned preparations, all % symbols refer to weight by weight percentage.

Particular compositions for use in the method of the present invention are those wherein the antagonist is formulated in vesicles such as liposome-containing compositions. Liposomes are vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If watersoluble materials are included in the aqueous phase during the swelling of the lipids they become entrapped in the aqueous layer between the lipid bilayers.

A particularly convenient method for preparing liposome formulated forms of hedgehog and ptc antagonists is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously. The single bilayered liposomes containing the encapsulated active ingredient can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of a hedgehog or ptc therapeutic. In some cases use may be made of plasters, bandages, dressings, gauze pads and the like which have been impregnated with a topical formulation containing the therapeutic formulation.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to another embodiment compositions containing a compound of this invention may also comprise an additional agent selected from the group consisting of corticosteroids, antiinflammatories, immunosuppressants, antimetabolites, and immunomodulators. Specific compounds within each of these classes may be selected from any of those listed under the appropriate group headings in "Comprehensive Medicinal Chemistry", Pergamon Press, Oxford, England, pp. 970-986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); steroids (inhaled, oral or topical) and interferons (immunomodulators).

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to produce the desired effects will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 50 mg/kg body weight per day of the active ingredient compound are useful. Most preferably, the antibody homlogs will be administered at a dose ranging between about 0.1 mg/kg body weight/day and about 20 mg/kg body weight/day, preferably ranging between about 0.1 mg/kg body weight/day and about 10 mg/kg body weight/day and at intervals of every 1-14 days. Preferably, an antibody composition is administered in an amount effective to provide a plasma level of antibody of at least 1 ug/ml.

Persons having ordinary skill in the art can readily test if an antagonist of the invention is having it intended effect. For instance, cells contained in a sample of the individual's epithelium are probed for the presence of the agent in vitro (or ex vivo) using a second reagent to detect the administered agent. For example, this may be a fluorochrome labelled antibody specific for the administered agent which is then measured by standard FACS (fluorescence activated cell sorter) analysis. Alternatively, presence of the administered agent is detected in vitro (or ex vivo) by the inability or decreased ability of the individual's cells to bind the same agent which has been itself labelled (e.g., by a fluorochrome). The preferred dosage should produce detectable coating of the vast majority of hedgehog-positive cells. Preferably, coating is sustained in the case of an antibody homolog for a 1-14 day period.

EXEMPLIFICATION

The invention now being generally described, it will be more readily understood by reference to the following examples which are included merely for purposes of illustration of certain aspects and embodiments of the present invention, and are not intended to limit the invention.

Example 1

Blockcade of Hair Follicle Morphogenesis in Mice Treated with AntiHedgehog Antibodies Materials and Methods Mice were obtained from Jackson Laboratory (Bar Harbor Maine) and Charles River Laboratories. Strains Balb/c and C57b1/6 were used. The data below are presented for the Balb/c strain only but results are similar for the other strain.

Anti-hedgehog antibody 5E1 was obtained using the methods described in Jessell et al., Cell, 87: 661 (1996). Anti-hedgehog antibodies AP.G6 and AC.D1 were obtained by immunizing mice with a sonic hedgehog:Fc fusion protein. Immunization took place i.p. at 7-29 day intervals and we then waited 20-30 days before the final boost i.v. with the same fusion protein. We then screened about 1000 primary clones using a sandwich ELISA with the hedgehog fusion protein and a sonic hedgehog direct ELISA.

We then screened the initial positives with a secondary screen consisting of the sandwich ELISA, immunohistochemical detection on COS cells expressing sonic hedgehog versus mock transfected COS cells; Sonic, Indian and Desert hedgehog direct ELISAs and FACS analysis on COS cells expressing Sonic hedgehog versus mock transfected COS cells and Sonic hedgehog-baculoviral transfected cells.

Of the positives obtained with this secondary screen, several were subcloned and the subclones rescreened as above.

A. Blockage of Hair Follicle Morphogenesis in Fetal Mice

We generated mice that lack bodycoat hair by treating pregnant mice with an anti-hedgehog antibody homolog. Histological analysis revealed the presence of normal placode and dermal papilla in these mice, yet the subsequent hairshaft formation was inhibited.

Maternal antibody treatment during embryogenesis has been employed to study the role of cell surface and secreted molecules during ontogeny. We took advantage of this approach to investigate the role of hedgehog in bodycoat hair follicle initiation and subsequent hair formation. Since body coat hair development in mice has been shown to initiate at embryonic day 13.5, E12.5 pregnant mice were injected with anti-hedgehog and control antibodies. Both the 5EI (Jessel et al., Cell 87: 661-673 (1996)) and APG-6 antibodies bind specifically to hedgehog family members and block their activity in vivo and in a 10T1/2 cell differentiation assay (see Table 1). An irrelevant isotype-matched antibody 1E6 ( Sultan et al., Nature, Biotechnology 15, 759-762 (1997) "Blockade of CD2-LFA-3 interactions protects human skin allografts in immunodeficient mouse/human chimeras") and the antibody AC.D1, which binds hedgeog proteins but does not block the differentiation of 10T1/2 cells were used as controls (see Table 1).

TABLE 1

| | Hedgehog Monoclonal Antibodies | | | |
| | Direct ELISA | | | 10T1/2 |
| Clone | Shh | Ihh | Dhh | Blocking |
| --- | --- | --- | --- | --- |
| 5E1 | +++ | +++ | + | ++ |
| AP.G6 | +++ | +++ | +/− | + |
| AC.D1 | +++ | ++ | + | − |
| IE6 | − | − | − | − |

Figure 1A:
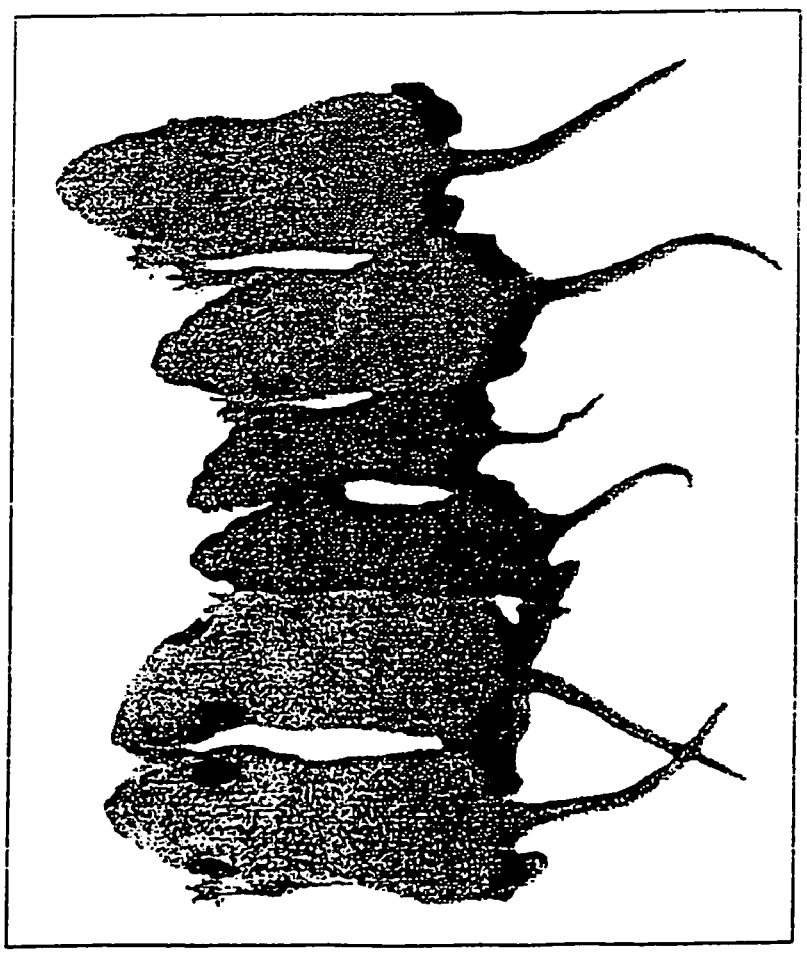
Figure 1F:
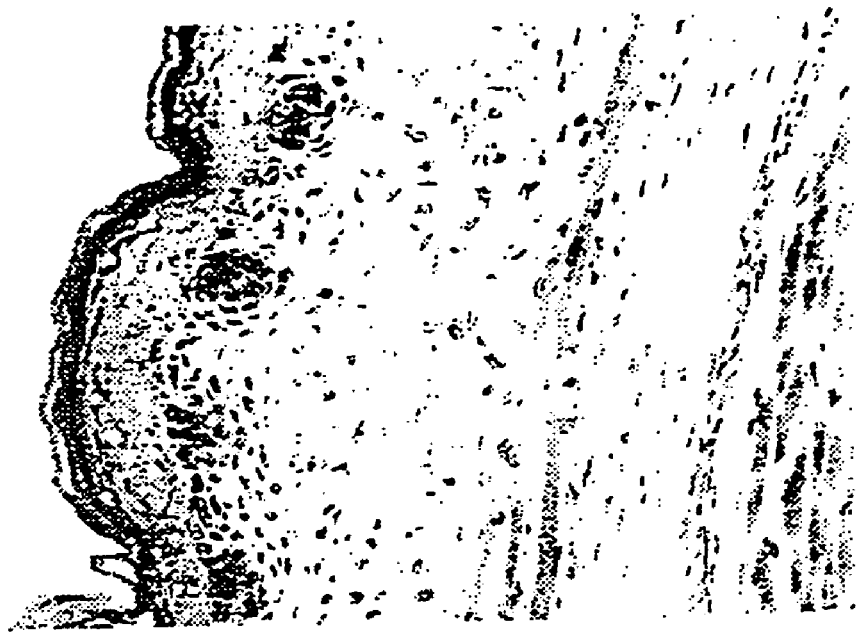
FIGS. 1E and 1F are histological sections through the epithelium of untreated mice and treated mice, respectively, at stage E18.5.
Figure 1E:
Figure 1H:
FIGS. 1G and 1H are histological sections through the epithelium of untreated mice and treated mice, respectively, at day 5 after birth.
Figure 1G:

Offspring of the 5EI and APG-6 antibody-treated mice were viable, however, the 5EI-treated neonates died within the first week after birth due to massive gastro-intestinal tract defects. The APG-6 treated mice were normal in size during the first week but gradually became runted. The cause of the lethality and runting in these mice is being investigated. Interestingly, an obvious and striking feature of these mice is that they lack bodycoat hair (FIG. 1A: 10 days) and maintained this hairless phenotype with continued antibody injection (FIG. 1B: 5 weeks). Histological analysis of the affected mice at development stage E15.5 reveals the appearance of epidermal placode and dermal condensation of mesenchymal cells (a precursor of dermal papilla) at the base of the placode comparable to that of the control mice (FIG. 1C and D). At E18.5, the epithelial cell-derived matrix cells underwent morphogenesis to form the inner root sheath in control mice (FIG. 1E). On the contrary, this process was absent in anti-hedgehog Ab treated mice (FIG. 1F) at the same stage and remained delayed throughout the first week of life (FIG. 1G and 1H, both for day 5 mice). Subsequently, matrix cells from the antibody treated mice with affected hair follicles were able to differentiate further into hair-shaft like structure, yet no hair was formed (FIG. 1I control: day 17 and FIG. 1J treatment: day 17). These data indicate that hedgehog is not required for initial placode and dermal papilla formation but is indispensable for the subsequent stage of matrix cell morphogenesis into hair.

Blockage in Older Fetal Mice

The hairless phenotype seen in the prenatal anti-hedgehog antibody homolog treated mice indicate that hedgehog is involved in the earliest hair-growing (anagen) phase during embryonic development. Each synchronized mouse hair cycle goes through three distinct phases around every three weeks after birth which comprise of the growing phase (anagen), the transitional phase (catagen) and the resting phase (telogen). In addition, the inhibition of hair growth is also observed in older mice treated with anti-hedgehog antibody homologs during the growing (anagen) phase of the hair cycle.

Figure 2:
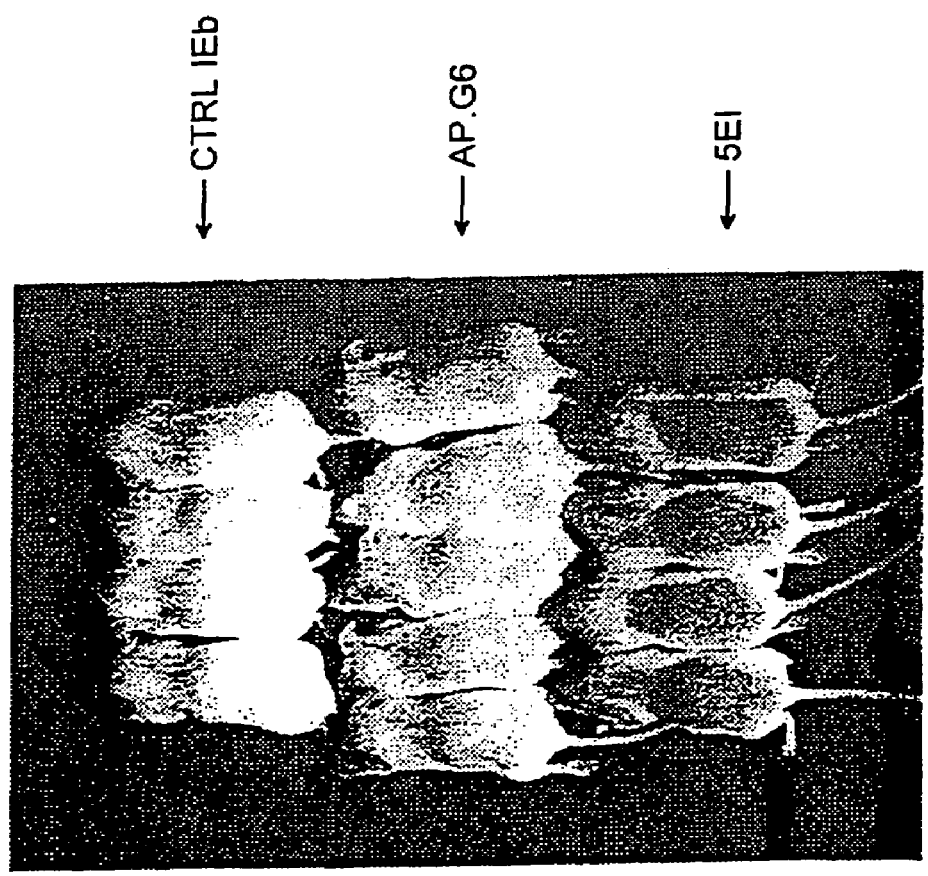
FIG. 2 is a picture of mice treated with control antibody or two different anti-hedgehog antibodies. One day before the backhair was shaved (at day 21), mice were treated and then treated every second day for an added period. Hair growth was delayed.

To assess whether the hedgehog pathway is involved in the anagen phase of subsequent hair cycles in older mice, anti-hedgehog antibodies were administered to mice at the stage of the second (3 weeks old) and fourth (9 weeks old) anagen phase of the hair growth cycle. To highlight the effect on hair growth, the backhair of these mice was shaven. The results showed that while the backhair of the control mice grew back completely within three weeks, the hair growth in anti-hedgehog antibody treated mice was completely blocked by 5EI and was delayed by APG6 treatment in both the 3 weeks and 9 weeks treatment groups (FIG. 2). The difference between the SEI and APG-6 antibody-treated mice might be due to the differences in the potency or half-life of these antibodies. The results demonstrate that hedgehog pathway is involve in general in the anagen hair growth phase in both juvenile and adult mice.

3. Blockage After Birth

Figure 3B:
FIG. 3B is a picture of 10-day old mice treated with anti-hedgehog antibody beginning on day 2 after birth.
Figure 3A:
FIG. 3A is a histological section through the epithelium of a two-day old mouse showing the beginning development of hair follicles.

We further demonstrate that hedgehog signaling is required to maintain hair morphogenesis by antibody administration at later developmental stages. To address whether hedgehog proteins are still required at a later stage after the initiation of the hair follicle morphogenesis process, mice were subjected to antibody treatment after birth, at which stage the hair follicle morphogenesis had begun (FIG. 3A). As shown in FIG. 3B. although there is formation of the bodycoat hair in anti-hedgehog antibody-treated mice, the hair is shorter, suggesting a delay of hair growth. The delay does not appear to result from overall developmental retardation in anti-hedgehog-antibody treated mice since many organs of these anti-hedgehog antibody treated mice display normal histology and maintain similar weight as control littermates (data not shown). Correlating with macroscopic observation, the anti-hedgehog antibody treated hair follicles are able to complete the morphogenesis process and form hair shaft by histological analysis (data not shown). Taken together, these data suggest that the hedgehog signaling pathway is required to maintain normal length of hair growth.

4. Reversal of Blockage

Figure 4A:
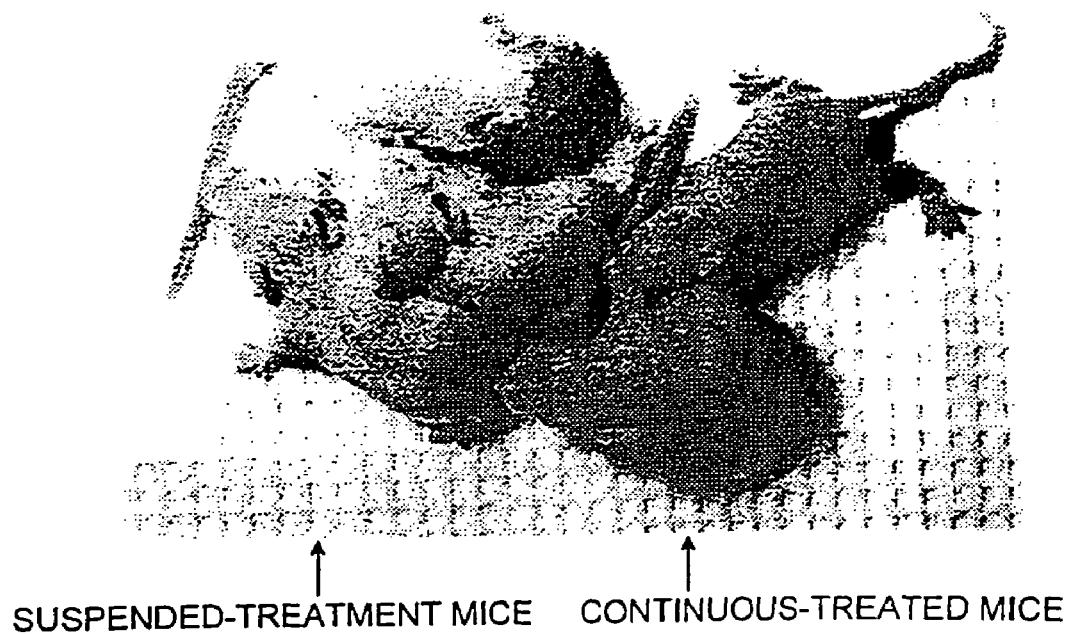
FIG. 4A is a picture of 12-day old mice, some of whom were: treated with control prenatally, treated prenatally but whose treatments were suspended: and continuously treated since before birth.

However, since these postnatal treated mice still form hair suggesting another independent pathway is also involved in later stages of hair growth. Moreover, the hairless phenotype can be reversed upon suspension of antibody treatment. To address whether the hairless phenotype can be reversed by withdrawal of antibody treatment, antibody treatments were suspended in some pups which had received antibodies prenatally. Macroscopically, at 12 days of age, these mice exhibited intermediate hair growth as compared to littermates continuously treated with anti-hedgehog antibodies and the control antibody-treated littermates (FIG. 4A: showing the mice resulting from control, continuous- and suspended-treatments). The delay in hair growth seen in these mice is most likely due to the blockade of hair follicle development as a result of the prenatal antibody treatment.

Figure 4B:
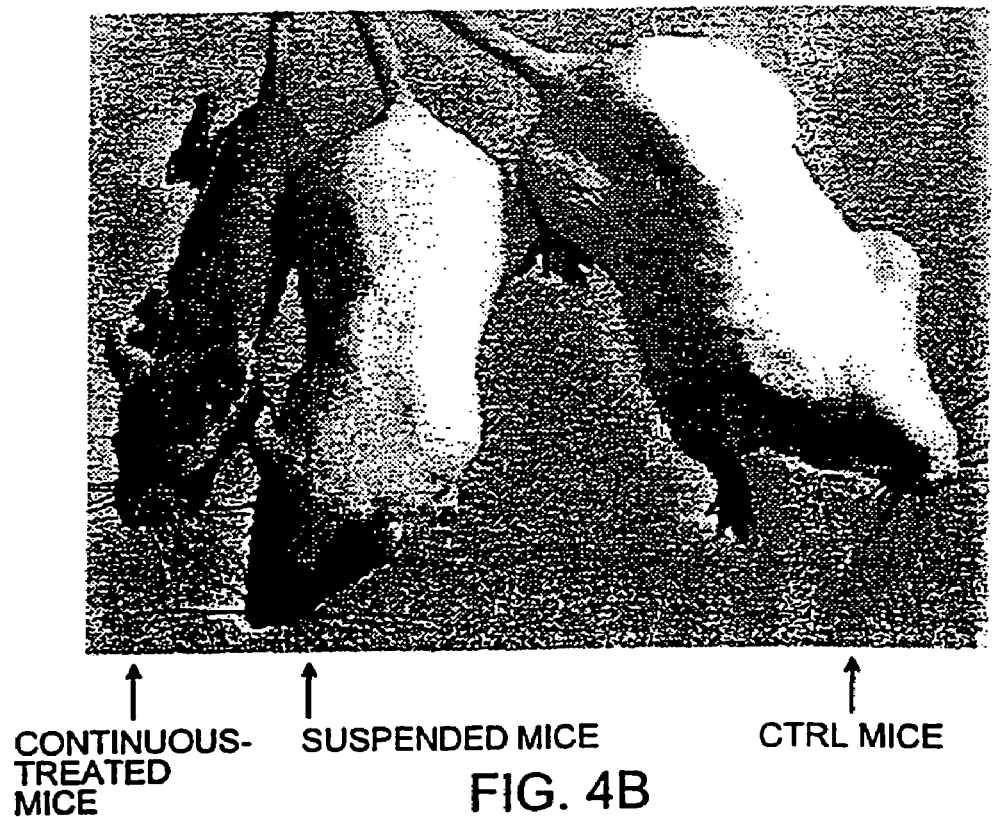
FIG. 4B is a picture of 5 week old mice showing no obvious difference between the control-treated mice and those mice treated prenatally but whose treatments were suspended.
Figures 5, 5A:
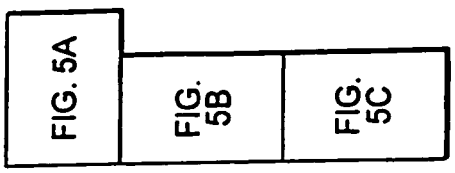

Indeed, by 4 weeks of age, there is no difference in the hair development between the anti-hedgehog antibody suspended mice and the control mice at both the macroscopic and histological levels ( FIG. 4B and data not shown). The reversibility of hair growth also is observed in mice which underwent continuous anti-hedgehog treatment until 2 and 8 weeks of age and were subsequently suspended from further treatment. (data not shown). These results indicate that both the hair matrix cells and dermal papilla cells were released from the previously blocked status and resume complete morphogenesis as soon as sufficient endogenous hedgehog signaling reoccurred, thus our data underscore a direct involvement of hedgehog-signaling pathway in hair formation.

Taken together, our results underscore a direct role of the hedgehog signaling pathway throughout each hair follicle morphogenesis during mouse hair growth cycles. Our system of generating an inducible and reversible hairless phenotype by anti-hedgehog antibody treatment will be valuable for studying the regulation and mechanism of hair growth cycles, and for defining processes of development and regeneration in other organs mediated by these morphogens.

Subject matter disclosed in this application was developed as part of a joint research agreement between Ontogeny, Inc. and Biogen, Inc. Curis, Inc. is the successor in interest to Ontogeny, Inc.

We claim:

1. A method for inhibiting growth or differentiation of an epithelial cell, comprising contacting at least an epithelial cell with an amount of an agent effective to inhibit at least one of the growth or differentiation of said epithelial cell, wherein said agent is an anti-hedgehog antibody, and wherein the anti-hedgehog antibody is selected from 5E1, a humanized anti-hedgehog antibody thereof, or fragments thereof.

2. The method of claim 1, wherein the anti-hedgehog antibody is a humanized anti-hedgehog antibody, or fragments thereof.

3. The method of claim 1, wherein the epithelial cell is a cutaneous epithelial cell.

4. The method of claim 1, wherein the epithelial cell is a mammalian epithelial cell.

5. The method of claim 1, wherein the epithelial cell is a dermal keratinocyte.

6. The method of claim 5, wherein the epithelial cell is a mammalian epithelial cell.

7. The method of claim 1, wherein the epithelial cell is a mucosal epithelial cell.

8. The method of claim 7, wherein the epithelial cell is a mammalian epithelial cell.

9. The method of claim 1, wherein the epithelial cell is an epitheial stem cell.

10. The method of claim 9, wherein the epithelial cell is a mammalian epithelial cell.

11. The method of claim 1, wherein the epithelial cell is a hair follicle stem cell.

12. The method of claim 1, wherein the anti-hedgehog antibody is 5E1.

13. The method of claim 1, wherein the epithelial cell is a mammalian epithelial cell.

14. A method for inhibiting growth of an epithelial tissue, comprising contacting at least the epithelial tissue with an amount of an agent effective to inhibit proliferation of at least the epithelial cells in the tissue, wherein the agent is an anti-hedgehog antibody, and wherein the anti-hedgehog antibody is selected from 5E1, a humanized anti-hedgehog antibody thereof, or fragments thereof.

15. The method of claim 14, wherein the anti-hedgehog antibody is a humanized anti-hedgehog antibody, or fragments thereof 16. The method of claim 14, wherein the epithelial tissue is an internal epithelial tissue.

17. The method of claim 16, wherein the internal epithelial tissue is intestinal lining.

18. The method of claim 17, wherein the epithelial tissue is mammalian tissue.

19. The method of claim 16, wherein the epithelial tissue is mammalian tissue.

20. The method of claim 16, wherein the epithelial tissue is vertebrate epithelial tissue.

21. The method of claim 14, wherein the epithelial tissue is mammalian tissue.

22. A method for inhibiting growth of hair on an animal, comprising administering to the animal an amount of an agent effective to inhibit growth of hair on said animal, wherein the agent is an anti-hedgehog antibody, which anti-hedgehog antibody inhibits proliferation of hair follicle keratinocytes, and wherein the anti-hedgehog antibody is selected from 5E1, a humanized anti-hedgehog antibody thereof, or fragments thereof.

23. The method of claim 22, wherein the anti-hedgehog antibody is a humanized anti-hedgehog antibody, or fragments thereof 24. The method of claim 22, wherein the anti-hedgehog antibody is 5E1.

25. The method of claim 22, wherein the anti-hedgehog antibody affects the anagen phase of the hair growth cycle.

26. The method of claim 22, wherein administering comprises topically administering.

27. The method of claims 2, 15, or 23, wherein the anti-hedgehog antibody binds to a Sonic hedgehog protein.

28. A method for inhibiting the proliferation of hair follicle cells, comprising topically contacting the cells with an amount of an agent effective to decrease the proliferation of the hair follicle cells, wherein the agent is an anti-Sonic hedgehog antibody, a humanized anti-Sonic hedgehog antibody thereof, or fragments thereof.

29. The method of claim 28, wherein the anti-hedgehog antibody is 5E1.

30. The method of claim. 28, wherein the anti-hedgehog antibody affects the anagen phase of the hair growth cycle.

31. A method for inhibiting growth or differentiation of an epithelial cell, comprising contacting at least an epithelial cell with an amount of an agent effective to inhibit at least one of the growth or differentiation of said. epithelial cell, wherein said agent is an anti-Sonic hedgehog antibody, a humanized anti-Sonic hedgehog antibody thereof, or fragments thereof.

32. The method of claim 31, wherein the epithelial cell is a cutaneous epithelial cell.

33. The method of claim 32, wherein the epithelial cell is a mammalian epithelial cell.

34. The method of claim 31, wherein the epithelial cell is a dermal keratinocyte.

35. The method of claim 34, wherein the epithelial cell is a mammalian epithelial cell.

36. The method of claim 31, wherein the epithelial cell is a mucosal epithelial cell.

37. The method of claim 36, wherein the epithelial cell is a mammalian epithelial cell.

38. The method of claim 31, wherein the epithelial cell is an epithelial stem cell.

39. The method of claim 38, wherein the epithelial cell is a mammalian epithelial cell.

40. The method of claim 31, wherein the epithelial cell is a hair follicle stem cell.

41. The method of claim 31, wherein the epithelial cell is an internal epithelial cell.

42. The method of claim 41, wherein the epithelial cell is a mammalian epithelial cell.

43. The method of claim 41, wherein the epithelial cell is a vertebrate epithelial cell.

44. The method of claim 31, wherein the epithelial cell is a mammalian epithelial cell.

45. A method for inhibiting growth of an epithelial tissue, comprising topically contacting at least the epithelial tissue with an amount of an agent effective to inhibit proliferation of at least the epithelial cells in the tissue, wherein the agent is an anti Sonic-hedgehog antibody, a humanized anti-Sonic hedgehog antibody thereof, or fragments thereof.

46. The method of claim 45, wherein the epithelial tissue is mammalian, tissue.

47. A method for inhibiting growth of hair on an animal, comprising administering to the animal an amount of an agent effective to inhibit growth of hair on said animal, which agent inhibits proliferation of hair follicle keratinocytes, wherein the agent is an anti-Sonic hedgehog antibody, a humanized anti-Sonic hedgehog antibody thereof, or fragments thereof.

48. A method for inhibiting growth or differentiation of a hair follicle stem cell, comprising contacting said cell with an amount of an agent effective to inhibit at least one of the growth or differentiation of said cell, wherein said agent is an anti-hedgehog antibody, and wherein the anti-hedgehog antibody is selected from 5E1, a humanized anti-hedgehog antibody thereof, or fragments thereof.

49. A method for inhibiting the proliferation of hair follicle cells, comprising topically contacting the cells with an amount of an agent effective to decrease the proliferation of the hair follicle cells, wherein the agent is an anti-hedgehog antibody selected from 5E1, a humanized anti-hedgehog antibody thereof, or fragments thereof.

50. A method for inhibiting growth of hair on an animal, comprising administering to the animal an amount of an agent effective to inhibit growth of hair on said animal, wherein the agent is an anti-hedgehog antibody, which anti-hedgehog antibody inhibits proliferation of hair follicle keratinocytes, and wherein the anti-hedgehog antibody is selected from an anti-Sonic hedgehog antibody, a humanized anti-Sonic hedgehog antibody thereof, or fragments thereof.

51. The method of claim 50, wherein administering comprises topically administering.

52. A method for inhibiting the proliferation of hair follicle cells, comprising topically contacting the cells with an amount of an agent effective to decrease the proliferation of the hair follicle cells, wherein the agent is an anti-hedgehog antibody selected from an anti-Sonic hedgehog antibody, a humanized anti-Sonic hedgehog antibody thereof, or fragments thereof.

* * * * *

UNITED STATES PATENT AND TRADEMARK OFFICE
CERTIFICATE OF CORRECTION

| | | |
|---|---|---|
| PATENT NO. | : 7,445,778 B2 | Page 1 of 1 |
| APPLICATION NO. | : 09/804490 | |
| DATED | : November 4, 2008 | |
| INVENTOR(S) | : Burkly et al. | |

It is certified that error appears in the above-identified patent and that said Letters Patent is hereby corrected as shown below:

In the Claims:

In claim 15, column 33, line 12, please change "thereof" to --thereof.--

In claim 23, column 33, line 35, please change "thereof" to --thereof.--

In claim 30, column 33, line 52, please change "claim. 28" to --claim 28--

In claim 31, column 33, line 57, please change "said. epithelial" to --said epithelial--

Signed and Sealed this

Twenty-first Day of April, 2009

JOHN DOLL
*Acting Director of the United States Patent and Trademark Office*

SEQUENCE LISTING

<160> NUMBER OF SEQ ID NOS: 1

<210> SEQ ID NO 1
<211> LENGTH: 176
<212> TYPE: PRT
<213> ORGANISM: Artificial Sequence
<220> FEATURE:
<223> OTHER INFORMATION: Consensus sequence of the N-terminal domain of
      vertebrate hedgehog protein
<220> FEATURE:
<221> NAME/KEY: MISC_FEATURE
<222> LOCATION: (6)..(6)
<223> OTHER INFORMATION: Xaa=Val or Gly
<220> FEATURE:
<221> NAME/KEY: MISC_FEATURE
<222> LOCATION: (7)..(7)
<223> OTHER INFORMATION: Xaa=Val, Phe or Pro
<220> FEATURE:
<221> NAME/KEY: MISC_FEATURE
<222> LOCATION: (8)..(8)
<223> OTHER INFORMATION: Xaa=Gly or Val
<220> FEATURE:
<221> NAME/KEY: MISC_FEATURE
<222> LOCATION: (9)..(9)
<223> OTHER INFORMATION: Xaa=Ser or Gly
<220> FEATURE:
<221> NAME/KEY: MISC_FEATURE
<222> LOCATION: (10)..(10)
<223> OTHER INFORMATION: Xaa=Arg or Lys
<220> FEATURE:
<221> NAME/KEY: MISC_FEATURE
<222> LOCATION: (13)..(13)
<223> OTHER INFORMATION: Xaa=Phe, His or Tyr
<220> FEATURE:
<221> NAME/KEY: MISC_FEATURE
<222> LOCATION: (14)..(14)
<223> OTHER INFORMATION: Xaa=Pro or Ala
<220> FEATURE:
<221> NAME/KEY: MISC_FEATURE
<222> LOCATION: (15)..(15)
<223> OTHER INFORMATION: Xaa=Arg or Lys
<220> FEATURE:
<221> NAME/KEY: MISC_FEATURE
<222> LOCATION: (17)..(17)
<223> OTHER INFORMATION: Xaa=any amino acid
<220> FEATURE:
<221> NAME/KEY: MISC_FEATURE
<222> LOCATION: (19)..(19)
<223> OTHER INFORMATION: Xaa=Val or Thr
<220> FEATURE:
<221> NAME/KEY: MISC_FEATURE
<222> LOCATION: (22)..(22)
<223> OTHER INFORMATION: Xaa=Ala or Leu
<220> FEATURE:
<221> NAME/KEY: MISC_FEATURE
<222> LOCATION: (27)..(27)
<223> OTHER INFORMATION: Xaa=Ser, Ile or Val
<220> FEATURE:
<221> NAME/KEY: MISC_FEATURE
<222> LOCATION: (29)..(29)
<223> OTHER INFORMATION: Xaa=Asn or Gly
<220> FEATURE:
<221> NAME/KEY: MISC_FEATURE
<222> LOCATION: (31)..(31)
<223> OTHER INFORMATION: Xaa=Pro or Ala
<220> FEATURE:
<221> NAME/KEY: MISC_FEATURE
<222> LOCATION: (41)..(41)
<223> OTHER INFORMATION: Xaa=Tyr or Ala
<220> FEATURE:
<221> NAME/KEY: MISC_FEATURE
<222> LOCATION: (45)..(45)
<223> OTHER INFORMATION: Xaa=Ile or Val
<220> FEATURE:
<221> NAME/KEY: MISC_FEATURE
<222> LOCATION: (46)..(46)

```
<223> OTHER INFORMATION: Xaa=Ala or Ser
<220> FEATURE:
<221> NAME/KEY: MISC_FEATURE
<222> LOCATION: (48)..(48)
<223> OTHER INFORMATION: Xaa=Ser, Asn or Gly
<220> FEATURE:
<221> NAME/KEY: MISC_FEATURE
<222> LOCATION: (54)..(54)
<223> OTHER INFORMATION: Xaa=Glu or Asp
<220> FEATURE:
<221> NAME/KEY: MISC_FEATURE
<222> LOCATION: (56)..(56)
<223> OTHER INFORMATION: Xaa=Thr or Val
<220> FEATURE:
<221> NAME/KEY: MISC_FEATURE
<222> LOCATION: (71)..(71)
<223> OTHER INFORMATION: Xaa=Thr or Ser
<220> FEATURE:
<221> NAME/KEY: MISC_FEATURE
<222> LOCATION: (79)..(79)
<223> OTHER INFORMATION: Xaa=Gln or Glu
<220> FEATURE:
<221> NAME/KEY: MISC_FEATURE
<222> LOCATION: (83)..(83)
<223> OTHER INFORMATION: Xaa=Asp or Glu
<220> FEATURE:
<221> NAME/KEY: MISC_FEATURE
<222> LOCATION: (84)..(84)
<223> OTHER INFORMATION: Xaa=Arg or Lys
<220> FEATURE:
<221> NAME/KEY: MISC_FEATURE
<222> LOCATION: (85)..(85)
<223> OTHER INFORMATION: Xaa=Leu or Val
<220> FEATURE:
<221> NAME/KEY: MISC_FEATURE
<222> LOCATION: (91)..(91)
<223> OTHER INFORMATION: Xaa=Ser or Ala
<220> FEATURE:
<221> NAME/KEY: MISC_FEATURE
<222> LOCATION: (95)..(95)
<223> OTHER INFORMATION: Xaa=Gln or Met
<220> FEATURE:
<221> NAME/KEY: MISC_FEATURE
<222> LOCATION: (114)..(114)
<223> OTHER INFORMATION: Xaa=Ser or Ala
<220> FEATURE:
<221> NAME/KEY: MISC_FEATURE
<222> LOCATION: (115)..(115)
<223> OTHER INFORMATION: Xaa=Glu or Gln
<220> FEATURE:
<221> NAME/KEY: MISC_FEATURE
<222> LOCATION: (116)..(116)
<223> OTHER INFORMATION: Xaa=Glu or Asp
<220> FEATURE:
<221> NAME/KEY: MISC_FEATURE
<222> LOCATION: (135)..(135)
<223> OTHER INFORMATION: Xaa=Asn or Ser
<220> FEATURE:
<221> NAME/KEY: MISC_FEATURE
<222> LOCATION: (139)..(139)
<223> OTHER INFORMATION: Xaa=Asn or Met
<220> FEATURE:
<221> NAME/KEY: MISC_FEATURE
<222> LOCATION: (157)..(157)
<223> OTHER INFORMATION: Xaa=Lys or Arg
<220> FEATURE:
<221> NAME/KEY: MISC_FEATURE
<222> LOCATION: (158)..(158)
<223> OTHER INFORMATION: Xaa=Ala or Asn
<220> FEATURE:
<221> NAME/KEY: MISC_FEATURE
<222> LOCATION: (160)..(160)
<223> OTHER INFORMATION: Xaa=Val or Ile
<220> FEATURE:
<221> NAME/KEY: MISC_FEATURE
<222> LOCATION: (162)..(162)
<223> OTHER INFORMATION: Xaa=Cys or Val
<220> FEATURE:
<221> NAME/KEY: MISC_FEATURE
```

```
<222> LOCATION: (166)..(166)
<223> OTHER INFORMATION: Xaa=Ser or Ala
<220> FEATURE:
<221> NAME/KEY: MISC_FEATURE
<222> LOCATION: (167)..(167)
<223> OTHER INFORMATION: Xaa=Glu or Asp
<220> FEATURE:
<221> NAME/KEY: MISC_FEATURE
<222> LOCATION: (168)..(168)
<223> OTHER INFORMATION: Xaa=His or Asn
<220> FEATURE:
<221> NAME/KEY: MISC_FEATURE
<222> LOCATION: (170)..(170)
<223> OTHER INFORMATION: Xaa=Ala, Val or Leu
<220> FEATURE:
<221> NAME/KEY: MISC_FEATURE
<222> LOCATION: (173)..(173)
<223> OTHER INFORMATION: Xaa=Lys or Arg
<220> FEATURE:
<221> NAME/KEY: MISC_FEATURE
<222> LOCATION: (174)..(174)
<223> OTHER INFORMATION: Xaa=Thr, Ser or Ala

<400> SEQUENCE: 1

Cys Gly Pro Gly Arg Xaa Xaa Xaa Xaa Xaa Arg Arg Xaa Xaa Xaa Lys
1               5                   10                  15

Xaa Leu Xaa Pro Leu Xaa Tyr Lys Gln Phe Xaa Pro Xaa Val Xaa Glu
            20                  25                  30

Lys Thr Leu Gly Ala Ser Gly Arg Xaa Glu Gly Lys Xaa Xaa Arg Xaa
        35                  40                  45

Ser Glu Arg Phe Lys Xaa Leu Xaa Pro Asn Tyr Asn Pro Asp Ile Ile
    50                  55                  60

Phe Lys Asp Glu Glu Asn Xaa Gly Ala Asp Arg Leu Met Thr Xaa Arg
65                  70                  75                  80

Cys Lys Xaa Xaa Xaa Asn Ser Leu Ala Ile Xaa Val Met Asn Xaa Trp
            85                  90                  95

Pro Gly Val Lys Leu Arg Val Thr Glu Gly Trp Asp Glu Asp Gly His
            100                 105                 110

His Xaa Xaa Xaa Ser Leu His Tyr Glu Gly Arg Ala Val Asp Ile Thr
    115                 120                 125

Thr Ser Asp Arg Asp Arg Xaa Lys Tyr Gly Xaa Leu Ala Arg Leu Ala
    130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa Xaa Ser Xaa Ala Ala Xaa Xaa Gly Gly
            165                 170                 175
```